US012779237B2

(12) United States Patent
Matsuo et al.

(10) Patent No.: US 12,779,237 B2
(45) Date of Patent: Nov. 3, 2026

(54) PLASMA TREATMENT DEVICE, IRRADIATION INSTRUMENT, AND IRRADIATION NOZZLE

(71) Applicant: SEKISUI CHEMICAL CO., LTD., Osaka (JP)

(72) Inventors: Tatsuya Matsuo, Kyoto (JP); Yu Nagahara, Kyoto (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 210 days.

(21) Appl. No.: 18/294,269

(22) PCT Filed: Aug. 2, 2022

(86) PCT No.: PCT/JP2022/029626
§ 371 (c)(1),
(2) Date: Feb. 1, 2024

(87) PCT Pub. No.: WO2023/013629
PCT Pub. Date: Feb. 9, 2023

(65) Prior Publication Data
US 2025/0090853 A1 Mar. 20, 2025

(30) Foreign Application Priority Data
Aug. 2, 2021 (JP) ................................ 2021-126712

(51) Int. Cl.
*A61N 1/44* (2006.01)

(52) U.S. Cl.
CPC ..................................... *A61N 1/44* (2013.01)

(58) Field of Classification Search
CPC ........ A61B 18/042; A61C 17/00; A61N 1/44; H05H 1/24; H05H 1/26
(Continued)

(56) References Cited

U.S. PATENT DOCUMENTS 5,843,079 A * 12/1998 Suslov ................. A61B 18/042 606/43
7,300,436 B2 * 11/2007 Penny .................. A61B 18/042 606/41
(Continued)

FOREIGN PATENT DOCUMENTS

CN 106231770 12/2016
CN 106572586 4/2017
(Continued)

OTHER PUBLICATIONS

International Search Report issued Sep. 13, 2022 in International Application No. PCT/JP2022/029626, with English translation.
(Continued)

*Primary Examiner* — Michael F Peffley
(74) *Attorney, Agent, or Firm* — Wenderoth, Lind & Ponack, L.L.P.

(57) ABSTRACT

An irradiation instrument includes an irradiation nozzle and an irradiation instrument main body. The irradiation instrument main body includes an inner electrode which is configured to apply voltage to a plasma generating gas and includes a plasma generation region for generating plasma. The irradiation nozzle includes a main tube formed of a non-conductive material, and a conductive part which covers all of an outer surface of the main tube and protrudes beyond a tip of the main tube in an axial direction of the main tube. The conductive part is configured to come into contact with a reactive gas discharged from the tip of the main tube, and discharge the reactive gas which includes at least one of plasma or a reactive species generated by the plasma.

7 Claims, 6 Drawing Sheets

(58) Field of Classification Search
USPC .......................................................... 606/40–50
See application file for complete search history.

(56) References Cited

U.S. PATENT DOCUMENTS

| | | | | |
|---|---|---|---|---|
| 8,994,271 | B2 * | 3/2015 | Kindel ................. | A61B 18/042 315/111.21 |
| 2011/0301412 | A1 | 12/2011 | Cho | |
| 2012/0187841 | A1 | 7/2012 | Kindel et al. | |
| 2012/0283732 | A1 * | 11/2012 | Lam ................. | A61B 17/00491 606/49 |
| 2013/0153545 | A1 | 6/2013 | Kim et al. | |
| 2019/0209854 | A1 * | 7/2019 | Nagahara ............... | A61C 19/06 |
| 2022/0053628 | A1 | 2/2022 | Itoh | |

FOREIGN PATENT DOCUMENTS

| | | |
|---|---|---|
| JP | 2010-85231 | 4/2010 |
| JP | 2013-501332 | 1/2013 |
| JP | 2014-66100 | 4/2014 |
| JP | 2019-217093 | 12/2019 |
| KR | 10-2009-0112831 | 10/2009 |
| KR | 10-2011-0134255 | 12/2011 |
| WO | 2012/153332 | 11/2012 |
| WO | 2019/160151 | 8/2019 |
| WO | 2020/246435 | 12/2020 |

OTHER PUBLICATIONS

Extended European Search Report issued Jul. 1, 2025 in corresponding European Patent Application No. 22853048.1.
Office Action dated Mar. 10, 2026 in Chinese Patent Application No. 202280053571.4, with English Translation of Search Report.

* cited by examiner

PLASMA TREATMENT DEVICE, IRRADIATION INSTRUMENT, AND IRRADIATION NOZZLE

CROSS-REFERENCE TO RELATED APPLICATION

Priority is claimed from Japanese Patent Application No. 2021-126712 filed on Aug. 2, 2021, the contents of which are incorporated herein by reference.

TECHNICAL FIELD

The present invention relates to a plasma treatment apparatus, an irradiation instrument, and an irradiation nozzle.

BACKGROUND ART

Medical plasma treatment devices are known that perform treatment, sterilization, etc. using plasma or reactive species generated by plasma. In medical plasma treatment devices, for example, plasma or a medical application gas (reactive gas) containing reactive species is irradiated or applied to an affected area to promote healing of an abnormality such as a wound.

However, when reactive gas is blown to an affected area, especially a sensitive area such as inside of the oral cavity, it may cause a prickling pain.

In particular, pain is likely to be caused when, in an attempt to enhance the effects of treatment or sterilization, the density of reactive species contained in the reactive gas is increased or the nozzle tip is brought closer to the affected area.

This pain is assumed to be caused by current leakage from the high-voltage electrode in the irradiation instrument of the plasma treatment device to the affected area via the conductive reactive gas. Another conceivable reason is that the affected area is overheated to about 50° C. during the plasma disappearance process.

For addressing this issue, Japanese Unexamined Patent Application Publication (Translation of PCT Application) No. 2013-501332 (hereinafter, "JP 2013-501332") proposes fitting a conductive cap having a slit to the front end of the irradiation nozzle.

Presumably, the conductive cap removes charge from the charged particles in the reactive gas, thereby allowing the plasma state to end within the cap. Further, it is presumed that the cap also removes heat from the reactive gas, and can thereby prevent overheating of the affected area.

CITATION LIST

Patent Literature

Patent Literature 1: Japanese Unexamined Patent Application Publication (Translation of PCT Application) No. 2013-501332

SUMMARY OF INVENTION

Technical Problem

However, as a result of intensive study by the present inventors, it has been found that since the reactive gas generated by plasma contains charged particles, when the reactive gas comes into contact with the conductive cap, the reactive species contained in the reactive gas are likely to be deactivated, resulting in less amount of reactive species transported to a target such as an affected area. Further, it has been found that there is a large gap between the cap of JP 2013-501332 and the irradiation nozzle, where the diffusion of reactive gas occurs, which also becomes a factor for deactivation of the reactive species.

Furthermore, when a cap is used as in 1JP 2013-501332, the tip of the irradiation instrument becomes thicker. This poses another problem that it becomes difficult to irradiate narrow areas such as inside of the oral cavity.

In view of the above circumstances, an object of the present invention is to provide a plasma treatment apparatus which can deliver a sufficient amount of reactive species to a target such as an affected area while suppressing pain inflicted on the target, as well as an irradiation instrument for the apparatus, and an irradiation nozzle used in the irradiation instrument.

Solution to Problem

Configurations adopted by the present invention in order to solve the above-mentioned problem are as enumerated below.

[1] An irradiation nozzle for discharging a reactive gas containing one or both of plasma and a reactive species generated by the plasma, comprising:

a main tube with its inner surface being at least partially formed of a non-conductive material; and a conductive part located at a tip of the main tube, wherein the conductive pan is positioned such that part or all of the conductive part comes into contact with the reactive gas discharged from the tip of the main tube.

[2] The irradiation nozzle according to [1], wherein the inner surface of the main tube is entirely formed of the non-conductive material.

[3] The irradiation nozzle according to [1] or [2], wherein the conductive part covers part or all of an outer surface of the main tube and protrudes beyond a tip of the main tube in an axial direction of the main tube.

[4] The irradiation nozzle according to any one of [1] to [3], wherein the main tube is formed of a transparent material, and at least part of an outer surface of the main tube is not covered with any material so as to form an exposed part exposed to outside of the main tube, so that an inside of the main tube is observable through the exposed part.

[5] The irradiation nozzle according to [4], wherein the conductive part covers all of the outer surface of the main tube except for the exposed part of the main tube and protrudes beyond a tip of the main tube in an axial direction of the main tube.

[6] The irradiation nozzle according to any one of [1] to [5], wherein the conductive part is grounded.

[6A] The irradiation nozzle according to any one of [1] to [6], wherein the electrical resistivity (measured value at 20° C.) of the non-conductive material is preferably $10^6$ Ωm or more, more preferably $10^{11}$ Ωm or more, even more preferably $10^{14}$ Ωm or more, and the electrical resistivity (measured value at 20° C.) of the conductive part is preferably $10^8$ to $10^2$ Ωm, more preferably $10^{-8}$ to $10^{-4}$ Ωm, even more preferably $10^{-8}$ to $10^{-7}$ Ωm.

[7] An irradiation instrument comprising the irradiation nozzle according to any one of [1] to [6A] and an irradiation instrument main body, wherein the irradiation instrument main body contains therein a plasma generation region where plasma is generated.

[8] The irradiation instrument according to [7], wherein the irradiation nozzle is detachable from the irradiation instrument main body.

[9]A plasma treatment apparatus comprising: the irradiation instrument according to [7] or [8]; a gas supply unit that supplies plasma generating gas to the irradiation instrument main body; and a power supply unit that supplies power to the irradiation instrument main body.

[10] An irradiation nozzle for discharging a reactive gas containing one or both of plasma and a reactive species generated by the plasma, comprising:

a main tube with its inner surface being at least partially formed of a non-conductive material; and a conductive part formed of a conductive material, wherein the conductive part satisfies one or both of (1) and (2):

(1) at least part of the conductive part is located at a tip of the main tube; and (2) the conductive part is located on part of the inner surface of the main tube.

[11] The irradiation nozzle according to [10], wherein the inner surface of the main tube is entirely formed of the non-conductive material.

[12] The irradiation nozzle according to [10] or [11], wherein the conductive part covers part or all of an end surface at the tip of the main tube or an outer surface of the main tube and has a protrusion protruding beyond the tip of the main tube in an axial direction of the main tube.

[13] The irradiation nozzle according to any one of [10] to [12], wherein the protrusion has an annular shape with its diameter decreasing toward an axial direction of the main tube.

[13A] The irradiation nozzle according to anyone of [10] to [13], wherein the electrical resistivity (measured value at 20° C.) of the non-conductive material is preferably $10^6$ Ωm or more, more preferably $10^{11}$ Ωm or more, even more preferably $10^{14}$ Ωm or more, and the electrical resistivity (measured value at 20° C.) of the conductive part is preferably $10^{-8}$ to $10^2$ Ωm, more preferably $10^{-8}$ to $10^{-4}$ Ωm, even more preferably $10^{-8}$ to $10^{-7}$ Ωm.

[14] An irradiation instrument comprising the irradiation nozzle according to any one of [10] to [13A] and an irradiation instrument main body, wherein the irradiation instrument main body contains therein a plasma generation region where plasma is generated.

[15] The irradiation instrument according to [14], wherein the irradiation nozzle has an attach-detach mechanism that is attached to and engages with the irradiation instrument main body, wherein a rear end of the main tube is in contact with a periphery of an opening at a tip of the irradiation instrument main body.

[16] A plasma treatment apparatus comprising: the irradiation instrument according to [14] or [15]; a gas supply unit that supplies plasma generating gas to the irradiation instrument main body; and a power supply unit that supplies power to the irradiation instrument main body.

Advantageous Effects of Invention

By the plasma treatment apparatus of the present invention as well as the irradiation instrument for the apparatus, and the irradiation nozzle used in the irradiation instrument, it is possible to deliver a sufficient amount of reactive species to a target such as an affected area while suppressing pain inflicted on the target.

DESCRIPTION OF EMBODIMENTS

<Irradiation Instrument and Irradiation Nozzle>

Figure 1:
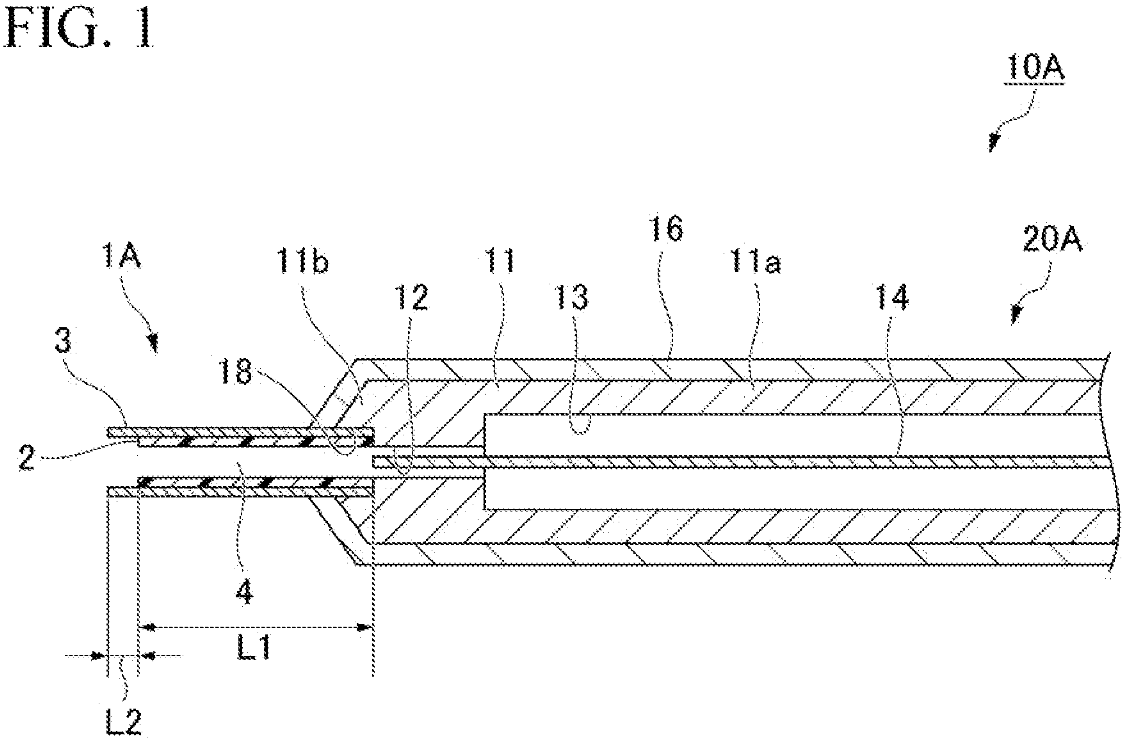
FIG. 1 is a partial cross-sectional view of an irradiation instrument according to a first embodiment of the present invention.

The irradiation instrument of the present invention comprises an irradiation nozzle and an irradiation instrument main body. The irradiation instrument main body contains therein a plasma generation region.

The plasma generation region is a space where plasma is generated. A reactive gas containing both or either one of the plasma generated in the plasma generation region and the reactive species generated by the plasma is discharged from the irradiation nozzle and blown to a target such as an affected area.

The irradiation nozzle of the present invention has a main tube with its inner surface being at least partially formed of a non-conductive material, and a conductive part located at the tip of the main tube. In this context, the expression "at least partially" for the inner surface means preferably 50% or more, more preferably 80% or more, even more preferably 99% or more of the total area of the inner surface of the main tube. Further, on the inner surface of the main tube, the portion formed of the non-conductive material may exist continuously or discontinuously. In terms of material availability and ease of manufacture, it is preferable that the entire inner surface (100%) of the main tube is formed of a non-conductive material.

Part or all of the conductive part is located so as to be in contact with the reactive gas discharged from the tip of the main tube. In this context, there is no particular restriction on the specific level of "part" of the conductive part as long as a sufficient area for contact with the reactive gas can be ensured.

In the irradiation nozzle of the present invention, the conductive part is preferably positioned so as to be in contact with or close to the tip of the main tube. By positioning the conductive part to be in contact with or close to the tip of the main tube, it is possible to prevent the reactive gas discharged from the tip of the main tube from diffusing before contacting the conductive pan. When the conductive part is positioned close to the tip of the main tube, the shortest distance between the tip of the main tube and the conductive part is preferably 5 mm or less, more preferably 1 mm or less.

Further, in the present specification and claims, the tip of each of the irradiation instrument, the irradiation instrument main body, and the irradiation nozzle means the end on the side from which reactive gas is discharged. Further, the end opposite to the tip, that is, the end to which gas is supplied may be referred to as the rear end.

Further, the conductive part contacting the tip of the main tube means that part of the conductive part is in contact with one or more of the end surface, outer surface, or inner surface at the tip of the main tube.

Further, in the present specification and claims, the term "plasma" means an ionized gas in which the molecules constituting the gas are ionized into positive ions and electrons and moving.

Furthermore, the reactive species means a highly chemically active gas containing any of radicals, excited atoms, excited molecules, ions, and the like.

In the present specification, a plasma generation region means a region where an electric field is concentrated and plasma is generated. The diameter of the plasma generation region means the diameter of the flow channel in the plasma generation region.

Further, in the present specification, the plasma generation unit means a part that allows a plasma generation region to be formed.

Hereinbelow, the irradiation nozzle according to embodiments of the present invention and the irradiation instrument provided with the irradiation nozzle are described with reference to the drawings. The drawings referred to in the following descriptions show characteristic parts enlarged for convenience, and the dimensional ratio, etc. of the components in the drawings may differ from the actual ones. Further, the materials, dimensions, etc. shown in the following descriptions are merely examples, and the present invention is not limited thereto, and may be modified as appropriate as long as the gist thereof is not altered.

First Embodiment

FIG. 1 is a partial cross-sectional view (longitudinal section) showing a plane along the axis of an irradiation nozzle 1A and an irradiation instrument 10A including the irradiation nozzle 1A according to the first embodiment of the present invention.

As shown in FIG. 1, the irradiation instrument 10A of the present embodiment includes an irradiation nozzle 1A and an irradiation instrument main body 20A.

The irradiation nozzle 1A is detachably connected to the irradiation instrument main body 20A.

The irradiation nozzle 1A is composed of a cylindrical main tube 2 and a cylindrical conductive part 3. The conductive part 3 covers the entire outer surface of the main tube 2 and is in contact with the entire outer surface of the main tube 2 (including the outer surface at the tip of the main tube 2).

The rear end of the conductive part 3 is aligned with the rear end of the main tube 2, and the tip of the conductive part 3 projects further in the axial direction of the main tube 2 than the tip of the main tube 2.

The main tube 2 in the present embodiment is entirely formed of a non-conductive material. Examples of non-conductive materials include, but are not limited to, insulators such as resins and ceramics.

Examples of resins include polyethylene, polypropylene, polyetheretherketone (PEEK), unilate, and fluororesin.

Examples of ceramics include alumina.

The electrical resistivity (measured value at 20° C.) of the non-conductive material forming the main tube 2 is preferably $10^{6}$ Ωm or more, more preferably $10^{11}$ Ωm or more, even more preferably $10^{14}$ Ωm or more. The upper limit of the electrical resistivity of the non-conductive material is not particularly limited as long as the material is available, but the range of the electrical resistivity is preferably $10^{6}$ to $10^{25}$ Ωm, more preferably $10^{11}$ to $10^{25}$ Ωm, even more preferably $10^{14}$ to $10^{25}$ Ωm. When the electrical resistivity of the non-conductive material in the main tube 2 is not less than the lower limit of the preferable range, it is possible to suppress deactivation of the reactive species due to trapping of electrons of the reactive gas. When the electrical resistivity of the non-conductive material in the main tube 2 is not more than the upper limit of the preferable range, the material can be easily obtained.

The material of the conductive part 3 is not particularly limited as long as it has conductivity. The electrical resistivity (measured value at 20° C.) of the conductive material forming the conductive part 3 is preferably $10^{-8}$ to $10^{2}$ Ωm, more preferably $10^{-8}$ to $10^{-4}$ μm, even more preferably $10^{-8}$ to $10^{-7}$ Ωm. When the electrical resistivity of the conductive material in the conductive part 3 is not more than the upper limit of the preferable range, it is easy to sufficiently suppress leakage current. When the electrical resistivity of the conductive material in the conductive part 3 is not less than the lower limit of the preferable range, it is possible to suppress deactivation of the plasma and the reactive species generated by the plasma.

For example, the conductive part 3 is formed of a conductive material such as a metal or a conductive carbon. There is no particular limitation with respect to the type of metal used for forming the conductive part 3, but a material with excellent corrosion resistance is preferable. Examples of materials with excellent corrosion resistance include stainless steel, copper, tungsten, and aluminum with a conductive alumite coating. Among them, stainless steel is preferable because it has excellent wear resistance as well.

Further, it is preferable that the conductive part 3 has an insulating layer on the outer surface and at the tip. That is, when the conductive part 3 is protected by an insulating layer at the outer surface and at the tip that may come into direct contact with the patient, electric shock to the patient can be prevented. The insulating layer is composed of an insulator. As the material of the insulator, materials used for general electric wire insulators such as thermosetting resins and thermoplastic resins may be used. Examples of the thermoplastic resin include polyethylene, polypropylene, polyvinyl chloride, polystyrene, acrylonitrile-butadiene-styrene resin (ABS resin), etc. Examples of the thermosetting resin include phenol resin, melamine resin, urea resin, epoxy resin, and unsaturated polyester resin, etc. Further, from the viewpoint of biocompatibility and flexibility, it is also a preferable embodiment to use polytetrafluoroethylene (PTFE) or silicone resin (silicone rubber). The thickness of the insulating layer is not particularly limited, but is preferably, for example, 0.1 mm to 2 mm, more preferably 0.5 mm to 1 mm.

The length L1 of the main tube 2 is preferably 1 to 40 mm, more preferably 5 to 15 mm. When the length L1 of the main tube 2 is not less than the lower limit of the preferable range, it is easy to deliver the reactive gas to the target. When the length L1 of the main tube 2 is not more than the upper limit of the preferable range, it is possible to suppress deactivation of the plasma and the reactive species generated by the plasma.

The length from the tip of the inner electrode 14 to the tip of the main tube 2 is preferably 5 to 50 mm, more preferably 20 to 30 mm. When the length is not less than the lower limit of the preferable range, it is easy to deliver the reactive gas to the target. When the length is not more than the upper limit of the preferable range, it is possible to suppress deactivation of the plasma and the reactive species generated by the plasma. That is, the energy of the discharged plasma can be further increased, or the concentration of the discharged reactive species can be further increased.

The inner diameter of the main tube 2 is preferably 1 to 10 mm, more preferably 2 to 5 mm. When the inner diameter of the main tube 2 is not less than the lower limit of the preferable range, a sufficient amount of reactive gas can be easily discharged. When the inner diameter of the main tube 2 is not more than the upper limit of the preferable range, it is possible to suppress deactivation of the plasma and the reactive species generated by the plasma.

The inner diameter of the main tube 2 is preferably 0.1 to 2 times the diameter of the plasma generation region, more preferably 0.2 to 1.5 times, even more preferably 0.3 to 0.9 times. When the inner diameter of the main tube 2 is not more than the upper limit of the preferable range relative to the diameter of the plasma generation region, it is possible to suppress deactivation of the plasma and the reactive species generated by the plasma. When the inner diameter of the main tube 2 is not less than the lower limit of the preferable range relative to the diameter of the plasma generation region, it is possible to avoid a decrease in the flow rate and flow velocity of the reactive gas due to pressure loss. Further, when the cross-section of the main tube 2 and the plasma generation region has a shape other than a circle, such as an ellipse or a polygon, the major axis of the ellipse or the diameter of the inscribed circle of the polygon may satisfy the above relationship.

When a wire-shaped electrode is used as the inner electrode 14 as in the present embodiment, an electric field is concentrated at the tip of the inner electrode 14 and plasma is generated. Therefore, the diameter of the plasma generation region in the present embodiment corresponds to the diameter of the flow channel at the tip of the inner electrode 14 (inner diameter of the cowling 11 at the tip of the inner electrode 14).

The wall thickness of the main tube 2 is preferably 100 to 3000 μm, more preferably 500 to 1500 μm. When the wall thickness of the main tube 2 is not less than the lower limit of the preferable range, it is easy to obtain the irradiation nozzle 1A with sufficient strength. When the wall thickness of the main tube 2 is not more than the upper limit of the preferable range, the reactive gas discharged from the tip of the main tube 2 can contact the conductive part 3 without excessively diffusing, and it is therefore possible to suppress deactivation of the plasma and the reactive species generated by the plasma.

The length L2 of the protrusion of the conductive portion 3 beyond the tip of the main tube 2 is preferably 0.1 mm to 20 mm, more preferably 1 mm to 5 mm. Further, depending on the design of the irradiation nozzle 1A, the length L2 is preferably 1 to 20 mm, more preferably 2 to 7 mm. When the protruding length L2 is not less than the lower limit of the preferable range, it is easy to sufficiently suppress leakage current. When the protruding length L2 is not more than the upper limit of the preferable range, it is possible to suppress deactivation of the plasma and the reactive species generated by the plasma.

Further, the ratio of L2 to L1 (L2/L1) is preferably 0.025 to 20, more preferably 0.05 to 1.

The thickness of the conductive part 3 is preferably 100 to 2000 μm, more preferably 500 to 1500 μm. When the thickness of the conductive part 3 is not less than the lower limit of the preferable range, the strength of the irradiation nozzle 1A can be further increased. When the thickness of the conductive part 3 is not more than the upper limit of the preferable range, it is possible to avoid the tip of the irradiation instrument 10A from becoming too thick.

Further, the conductive portion 3 may be provided with its part embedded in the wall portion of the main tube 2. In this case, the total thickness of the conductive part 3 and the wall of the main tube 2 at the location where the conductive part 3 is present is preferably 100 to 3000 μm, more preferably 500 to 1500 μm.

The irradiation instrument main body 20A can be roughly described as being composed of a cowling 11, an inner electrode 14, and an exterior material 16.

The cowling 11 includes an elongated cylindrical body section 11*a* and a head section 11*b* that closes the tip of the body section 11*a*. The body section 11*a* is not limited to one having a cylindrical shape, but may be an elliptical cylinder, a polygonal cylinder such as a square cylinder, a hexagonal cylinder, an octagonal cylinder, or the like.

On the inside of the body 1*a*, a small-diameter flow channel 12 and a large-diameter flow channel 13 larger in diameter than the small-diameter flow channel 12, both having a tubular shape (e.g., cylindrical shape), are formed coaxially with the outer periphery of the cowling 11 in this order as viewed from the tip side. A gas pipe is to be connected to the rear end of the large-diameter flow channel 13.

The size of the body 11*a* is not particularly limited, and may be set to a size that allows easy holding with fingers.

The head section 11*b* gradually narrows toward the tip thereof. That is, the head section 11*b* in the present embodiment has a conical shape. The head section 11*b* is not limited to that of a conical shape, and may be of a polygonal cone shape such as a quadrangular pyramid shape, a hexagonal pyramid shape, an octagonal pyramid shape or the like. The irradiation nozzle 1A is detachably attached to the head section 11*b*.

A cylindrical fitting hole 18 is formed inside the head section 11*b*. The fitting hole 18 is a hole that receives the irradiation nozzle 1A. The diameter of the fitting hole 18 is slightly larger than the diameter of the small-diameter flow channel 12, so that the irradiation nozzle 1A being inserted stops at a step formed between the fitting hole 18 and the small-diameter flow channel 12.

The material of the cowling 11 is not particularly limited, and the cowling 11 may be a one-piece molded product integrally formed as a whole or may be formed by combining multiple parts. Further, when it is formed by combining multiple parts, the parts may be made of the same material or different materials. Moreover, a part or all of the cowling 11 may have a multilayer structure.

For insulating the exterior material 16, the outer surface of the cowling 11 that comes into contact with the exterior material 16 is preferably formed of a non-conductive material.

Further, the inner surface of the portion where the small-diameter flow channel 12 is formed is also preferably formed of a non-conductive material so as not to deactivate the plasma.

Furthermore, the inner surface of the portion where the fitting hole 18 is formed is preferably formed of a material that has excellent wear resistance and corrosion resistance. Examples of materials excellent in wear resistance and corrosion resistance include metals such as stainless steel, and nonmetallic materials.

The inner electrode 14 is a rod-shaped electrode that is inserted from the rear end of the cowling 11 and inserted into the small-diameter flow channel 12 along the axis of the cowling 11.

The material of the inner electrode 14 is not particularly limited as long as the material is conductive, and any material that can be used for electrodes of known plasma generators can be used. Specific examples thereof include metals such as stainless steel, copper and tungsten, and carbon.

The outer diameter of the inner electrode 14 is preferably 1 to 10 mm, more preferably 1 to 3 mm. When the outer diameter of the inner electrode 14 is not less than the lower limit of the preferable range, local concentration of the electric field can be avoided and the durability of the electrode can be increased. Further, the discharge area is increased so that the amount of reactive gas discharged can be increased. When the outer diameter of the inner electrode 14 is not more than the upper limit of the preferable range, it is possible to prevent the entire irradiation instrument 10A from becoming too thick.

The inner electrode 14 functions as an application electrode that applies voltage to the plasma generating gas when connected to the power supply unit and supplied with power.

The exterior material 16 is connected to a ground wire of the power supply unit and functions as a ground electrode. As the exterior material 16, metals such as stainless steel, aluminum, and copper can be used, for example.

When the exterior material 16 functions as a ground electrode, it is possible to block electromagnetic waves generated from inside the cowling 1I and from electricity supply lines (cables, etc.). Further, when the exterior material 16 functions as a ground electrode, the conductive part 3 can be easily grounded.

In the present embodiment, when the irradiation nozzle 1A is inserted into the fitting hole 18, the outer surface of the conductive part 3 comes into contact with the exterior material 16.

The exterior material 16 has a one-piece structure covering both the body 11*a* and the head 11*b* of the cowling 11, and is detachably attached to the cowling 11. Alternatively, the exterior material 16 may be non-detachably fixed to the cowling 11.

With respect to the irradiation instrument 10A of the present embodiment, when the plasma generating gas is introduced from the rear end of the large-diameter flow channel 13 and a voltage is applied by the inner electrode 14, a plasma generation region is formed near the small-diameter flow channel 12, and plasma is generated. That is, the inner electrode 14 functions as a plasma generating unit for forming a plasma region.

The plasma generates reactive species, and a reactive gas containing one or both of plasma and a reactive species generated by the plasma is generated.

The reactive gas is allowed to pass through the reactive gas flow channel 4 in the irradiation nozzle 1A and is discharged and blown to the target, but since most of the inner surface of the irradiation nozzle 1A is the inner surface of the main tube 2 formed of a non-conductive material, the charged particles in the reactive gas are less likely to lose their charge. Moreover, since the conductive part 3 is connected to the tip of the main tube 2, the reactive gas is not allowed to diffuse before coming into contact with the conductive part 3. Therefore, the density of reactive species in the discharged reactive gas can be further increased.

Further, since the conductive part 3 is integrated with the main tube 2, it is possible to avoid the tip of the irradiation instrument from becoming thick.

Further, when the reactive gas comes into contact with the conductive part 3 at the outlet of the irradiation nozzle 1A, the electric charge of the reactive gas is removed. When the electric charge is removed, current does not leak to the irradiation target, and pain given to the affected area can be suppressed. In particular, when the irradiation nozzle 1A is attached to the irradiation instrument main body 20A, the conductive part 3 contacts the exterior material 16 and is thereby grounded, which provides a greater effect of removing the electric charge from the reactive gas and suppressing leakage current.

Further, when the conductive part 3 is formed of metal, the conductive part 3 generally has a high thermal conductivity as well, so that contact with the conductive part 3 is considered to provide another effect of removing heat from the reactive gas.

When the reactive gas comes into contact with the conductive part 3, some of the electrically charged particles of the plasma are lost. However, when the length of the conductive part 3 protruding from the main tube 2 is adjusted to sufficiently shorten the duration of contact between the reactive gas and the conductive part 3, it is possible to suppress the deactivation of reactive species (excited atoms, etc.) generated by plasma.

Thus, it is possible not only to suppress the pain inflicted on the target, such as the affected area, but also to deliver a sufficient amount of the reactive species to the target.

Second Embodiment

Figure 2:
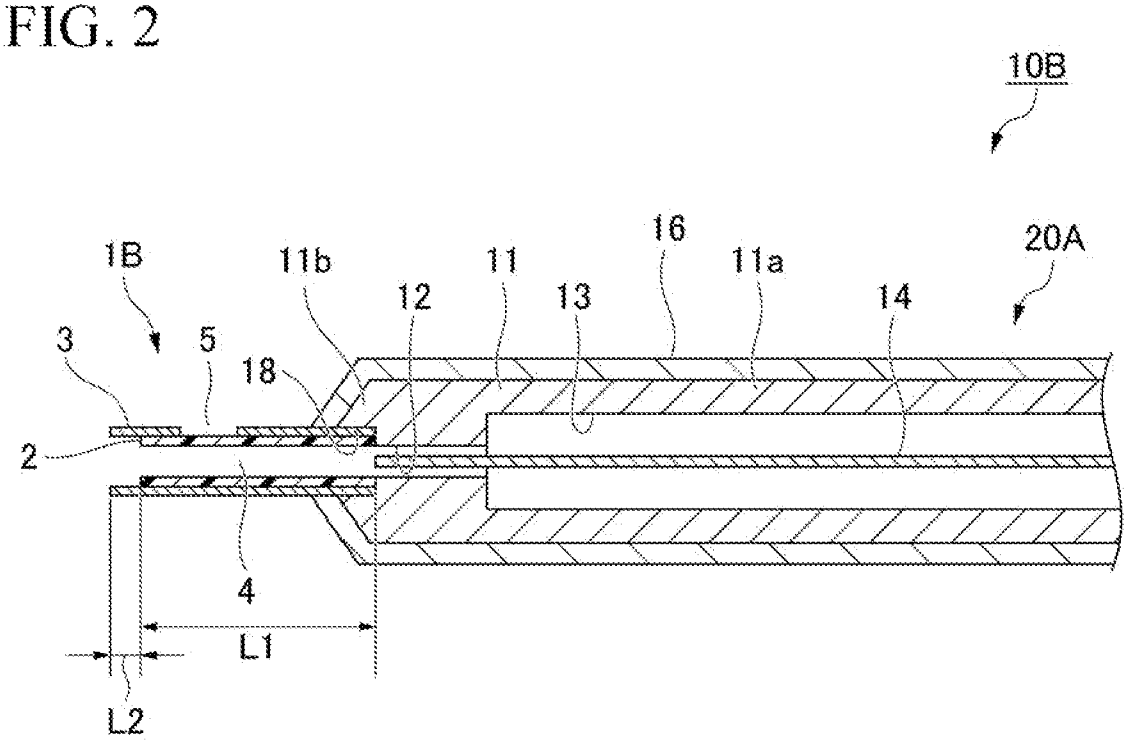
FIG. 2 is a partial cross-sectional view of an irradiation instrument according to a second embodiment of the present invention.

FIG. 2 is a partial cross-sectional view (longitudinal section) showing a plane along the axis of an irradiation nozzle 1B and an irradiation instrument 10B including the irradiation nozzle 1B according to the second embodiment of the present invention.

As shown in FIG. 2, the irradiation instrument 10B of the present embodiment includes an irradiation nozzle 1B and an irradiation instrument main body 20A, which is the same as the irradiation instrument main body 20A in the first embodiment.

The irradiation nozzle 1B is composed of a cylindrical main tube 2 and a cylindrical conductive part 3 with a hole at the exposed part 5. The conductive part 3 covers the entire outer surface of the main tube 2 except for the exposed part 5, and is in contact with the entire outer surface of the main tube 2 except for the exposed part 5 (including the outer surface at the tip of the main tube 2).

The rear end of the conductive part 3 is aligned with the rear end of the main tube 2, and the tip of the conductive part 3 projects further in the axial direction of the main tube 2 than the tip of the main tube 2.

The shape of the exposed part 5 is not particularly limited, and may be circular or rectangular, for example. The exposed part 5 may also be annular or spiral along the circumferential direction. When the exposed part 5 has an annular shape, it is preferable that it is not a closed annular shape but an open annular shape with its part cut open. The closed annular shape is not preferable in that electrical continuity between the tip of the conductive part 3 and the rear end of the conductive part 3 that is grounded to the exterior material 16 is interrupted.

The main tube 2 in the present embodiment is formed of a transparent non-conductive material. Examples of transparent non-conductive materials include polyethylene, a copolymer of tetrafluoromethylene and perfluoroalkoxyethylene (PFA), polycarbonate, polystyrene, polymethyl methacrylate, polyvinyl alcohol, and quartz glass.

The main tube 2 in the present embodiment is the same as the main tube 2 in the first embodiment except that transparency is required, and the preferred examples thereof are also the same as in the first embodiment; therefore, detailed descriptions are omitted.

The conductive part 3 is the same as the conductive part 3 in the first embodiment except that a hole is formed at the exposed pan 5, and the preferred examples thereof are also the same as in the first embodiment; therefore, detailed descriptions are omitted.

In the present embodiment, the main tube 2 formed of a transparent non-conductive material is exposed to the outside at the exposed part 5 without covered with other parts such as the conductive part 3, so that the inside of the main pipe 2 can be observed. This allows confirmation of plasma generation by the light inside the main tube 2.

Other technical effects are the same as in the first embodiment.

The area of the exposed part 5 is not particularly limited as long as the above observation is possible, but is preferably 25% or more, more preferably 50% or more, of the area of the outer surface of the main tube 2. The upper limit of the area of the exposed part 5 is not particularly limited as long as no problem arises from the aspect of design of the irradiation nozzle 1B, such as fixation of the conductive part 3.

Third Embodiment

Figure 3:
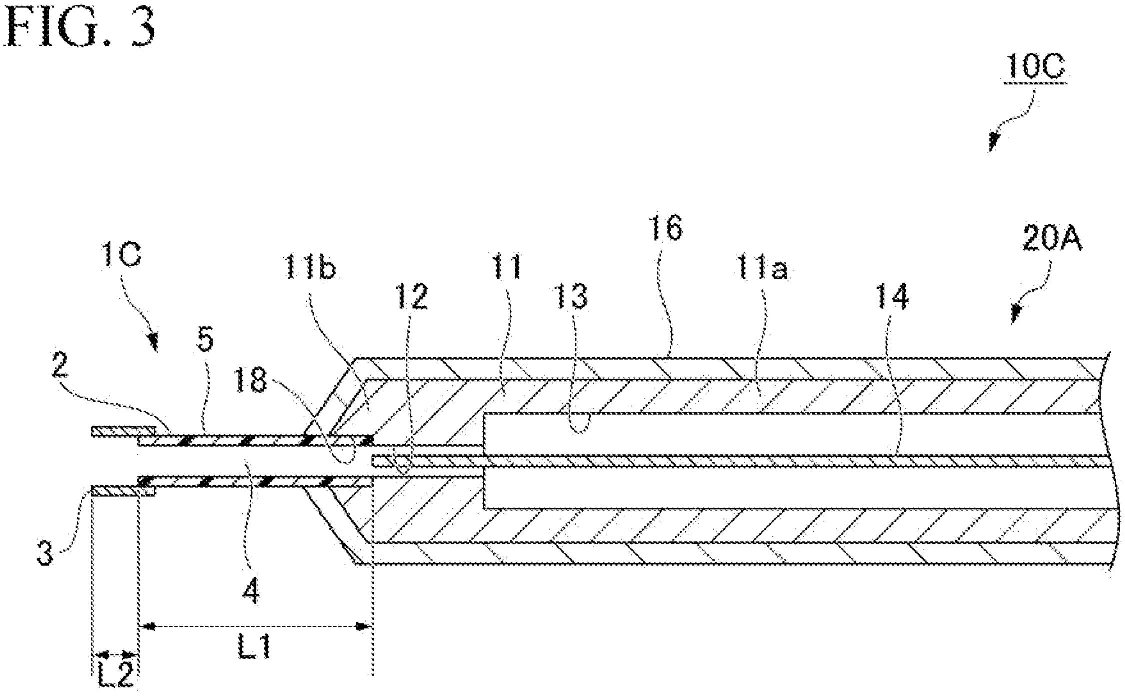
FIG. 3 is a partial cross-sectional view of an irradiation instrument according to a third embodiment of the present invention.

FIG. 3 is a partial cross-sectional view (longitudinal section) showing a plane along the axis of an irradiation nozzle 1C and an irradiation instrument 10C including the irradiation nozzle 1C according to the third embodiment of the present invention.

As shown in FIG. 3, the irradiation instrument 10C of the present embodiment includes an irradiation nozzle 1C and an irradiation instrument main body 20C, which is the same as the irradiation instrument main body 20A in the first embodiment.

The irradiation nozzle 1C is composed of a cylindrical main tube 2 and a short cylindrical conductive part 3. The rear end of the conductive part 3 is fitted around the tip of the main tube 2. That is, the rear end of the conductive part 3 is in contact with the outer surface at the tip of the main tube 2.

The main tube 2 in the present embodiment may be formed of a transparent non-conductive material or an opaque non-conductive material. When the main tube 2 is formed of a transparent non-conductive material, the portion around which the conductive part 3 is not fitted and which is not inserted into the irradiation instrument main body 20A becomes an exposed part 5 through which the inside of the main tube 2 can be observed.

The main tube 2 in the present embodiment is the same as the main tube 2 in the first embodiment except that transparency is preferred, and the preferred examples thereof are also the same as in the first embodiment; therefore, detailed descriptions are omitted. As regards the type of metal used for forming the conductive part 3, the same descriptions as for the conductive part 3 of the first embodiment apply.

The length L2 of the protrusion of the conductive portion 3 beyond the tip of the main tube 2 is preferably 1 to 20 mm, more preferably 2 to 7 mm. When the protruding length L2 is not less than the lower limit of the preferable range, it is easy to suppress leakage current. When the protruding length L2 is not more than the upper limit of the preferable range, it is possible to suppress deactivation of the plasma and the reactive species generated by the plasma.

Further, the length of the overlapping portion between the rear end of the conductive part 3 and the tip of the main tube 2 is not particularly limited as long as the conductive part 3 is securely fixed to the tip of the main tube 2.

The thickness of the conductive part 3 is preferably 100 to 2000 μm, more preferably 500 to 1500 μm. When the thickness of the conductive part 3 is not less than the lower limit of the preferable range, it is easy to maintain the strength of the conductive part 3. When the thickness of the conductive part 3 is not more than the upper limit of the preferable range, it is possible to avoid the tip of the irradiation instrument 10C from becoming too thick.

The technical effects of the present embodiment are similar to those of the first embodiment, but since the conductive part 3 cannot be connected to the exterior material 16 and grounded, the first embodiment is superior in the effect of suppressing leakage current.

The conductive part 3 may be connected to the exterior material 16 using a separate electric wire, or may be directly connected to the ground wire.

Fourth Embodiment

Figure 4:
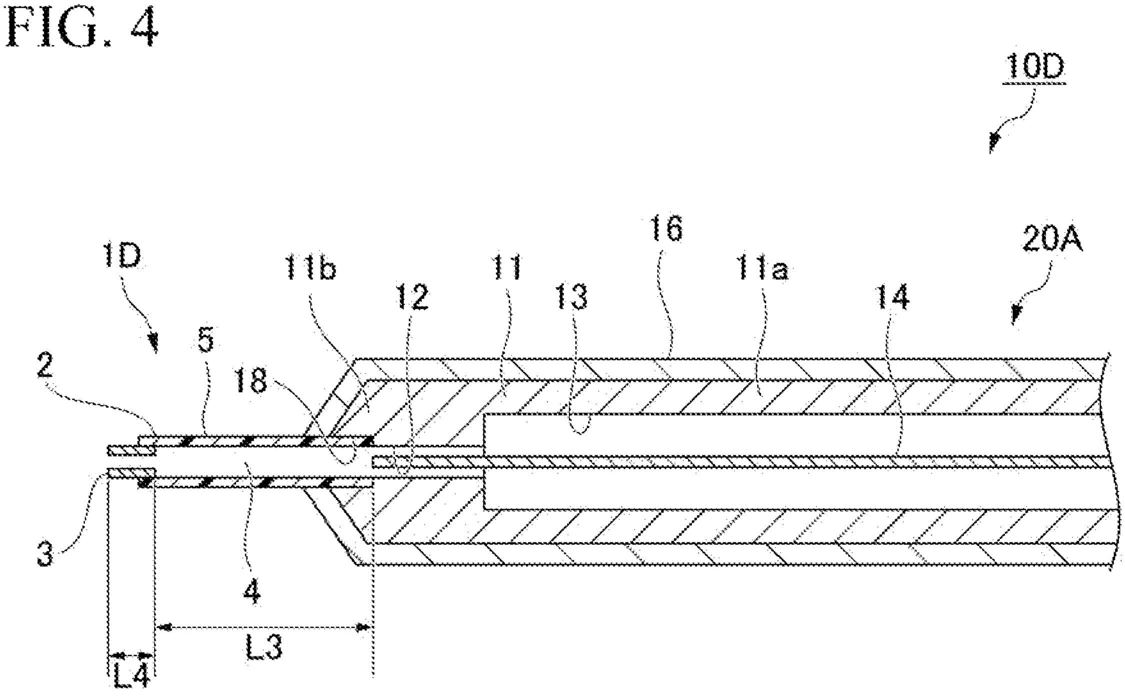
FIG. 4 is a partial cross-sectional view of an irradiation instrument according to a fourth embodiment of the present invention.

FIG. 4 is a partial cross-sectional view (longitudinal section) showing a plane along the axis of an irradiation nozzle 1D and an irradiation instrument 10D including the irradiation nozzle 1D according to the fourth embodiment of the present invention.

As shown in FIG. 4, the irradiation instrument 10D of the present embodiment includes an irradiation nozzle 1D and an irradiation instrument main body 20A, which is the same as the irradiation instrument main body 20A in the first embodiment.

The irradiation nozzle 1D is composed of a cylindrical main tube 2 and a short cylindrical conductive part 3. The rear end of the conductive pan 3 is inserted into the tip of the main tube 2. That is, the rear end of the conductive part 3 is in contact with the inner surface at the tip of the main tube 2.

In FIG. 4, the tip of the conductive pan 3 may protrude beyond the tip of the main tube 2 in the axial direction of the main tube 2, or may be aligned with the tip of the main tube 2. When the tip of the conductive part 3 is aligned with the tip of the main tube 2, the conductive part 3 may be a thin film such as a metal plating.

The main tube 2 in the present embodiment may be formed of a transparent non-conductive material or an opaque non-conductive material. When the main tube 2 is formed of a transparent non-conductive material, its portion into which the conductive part 3 is not inserted and which is not inserted into the irradiation instrument main body 20A becomes an exposed part 5 through which the inside of the main tube 2 can be observed.

The length L3 of the portion of the main tube 2 that is not in contact with the conductive pan 3 is preferably 1 to 40 mm, more preferably 5 to 15 mm. When the length L3 of the portion of the main tube 2 that is not in contact with the conductive part 3 is not less than the lower limit of the preferable range, it is easy to deliver the reactive gas to the target. When the length L3 of the portion of the main tube 2 that is not in contact with the conductive part 3 is not more the upper limit of the preferable range, it is possible to suppress deactivation of the plasma and the reactive species generated by the plasma.

The main tube 2 in the present embodiment is the same as the main tube 2 in the first embodiment except that transparency is preferred and except for the length L3 of the portion of the main tube 2 that is not in contact with the conductive part 3, and the preferred examples thereof are also the same as in the first embodiment; therefore, detailed descriptions are omitted. As regards the type of metal used for forming the conductive part 3, the same descriptions as for the conductive part 3 of the first embodiment apply.

The length L4 of the conductive part 3 is preferably 1 to 20 mm, more preferably 2 to 7 mm. When the length LA of the conductive part 3 is not less than the lower limit of the preferable range, it is easy to suppress leakage current. When the length LA of the conductive part 3 is not more than the upper limit of the preferable range, it is possible to suppress deactivation of the plasma and the reactive species generated by the plasma.

Further, the ratio of L4 to L3 (L4/L3) is preferably 0.025 to 20, more preferably 0.05 to 1.

The thickness of the conductive pan 3 is preferably 100 to 1000 μm, more preferably 100 to 500 μm. When the thickness of the conductive part 3 is not less than the lower limit of the preferable range, it is easy to maintain the strength of the conductive part 3. When the thickness of the conductive part 3 is not more than the upper limit of the preferable range, it is possible to allow a sufficient amount of the reactive gas to easily pass through the reactive gas flow channel 4.

The technical effects of the present embodiment are similar to those of the first embodiment, but since the conductive part 3 cannot be connected to the exterior material 16 and grounded, the first embodiment is superior in the effect of suppressing leakage current.

The conductive part 3 may be connected to the exterior material 16 using a separate electric wire, or may be directly connected to the ground wire.

Fifth Embodiment

Figure 5:
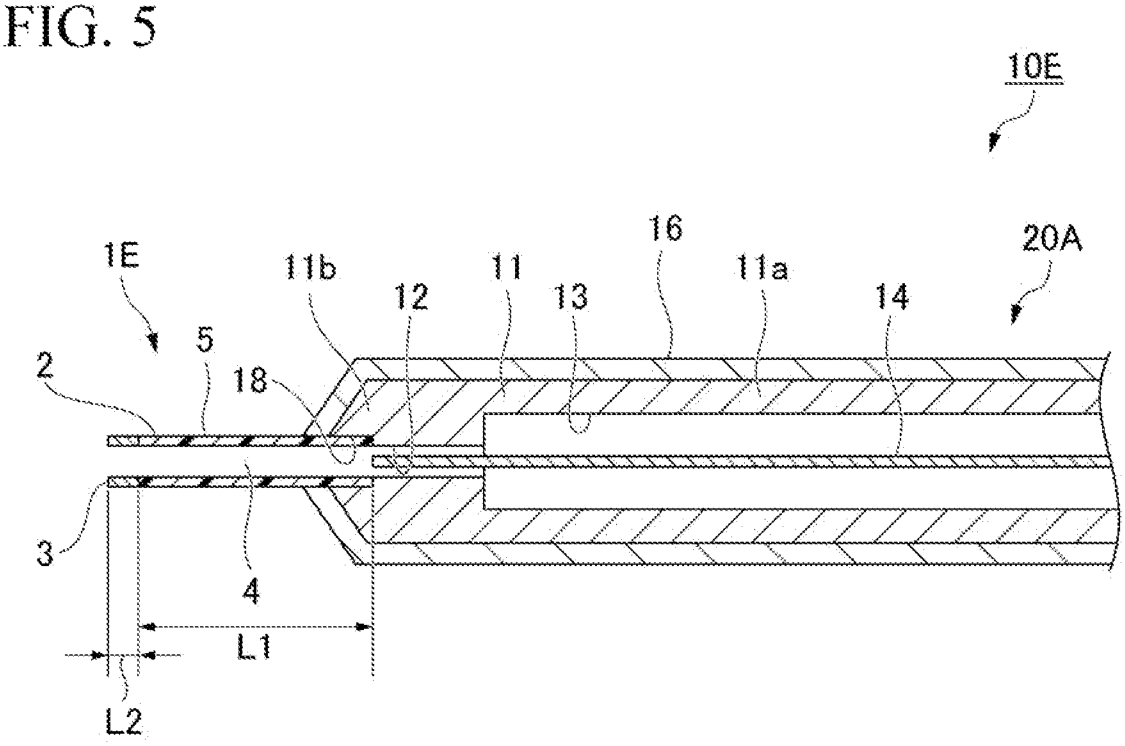
FIG. 5 is a partial cross-sectional view of an irradiation instrument according to a fifth embodiment of the present invention.

FIG. 5 is a partial cross-sectional view (longitudinal section) showing a plane along the axis of an irradiation nozzle 1E and an irradiation instrument 10E including the irradiation nozzle 1E according to the fifth embodiment of the present invention.

As shown in FIG. 5, the irradiation instrument 10E of the present embodiment includes an irradiation nozzle 1E and an irradiation instrument main body 20A, which is the same as the irradiation instrument main body 20A in the first embodiment.

The irradiation nozzle 1E is composed of a cylindrical main tube 2 and a short cylindrical conductive part 3. The mar end of the conductive part 3 is connected to the tip of the main tube 2. That is, the rear end of the conductive part 3 is in contact with the end surface at the tip of the main tube 2. In addition, the conductive part 3 is spaced apart from the exterior material 16.

The main tube 2 in the present embodiment may be formed of a transparent non-conductive material or an opaque non-conductive material. When the main tube 2 is formed of a transparent non-conductive material, its portion which is not inserted into the irradiation instrument main body 20A becomes an exposed part 5 through which the inside of the main tube 2 can be observed.

The main tube 2 in the present embodiment is the same as the main tube 2 in the first embodiment except that transparency is preferred, and the preferred examples thereof are also the same as in the first embodiment; therefore, detailed descriptions are omitted. As regards the type of metal used for forming the conductive part 3, the same descriptions as for the conductive part 3 of the first embodiment apply.

The length L2 of the conductive part 3 is preferably 1 to 20 mm, more preferably 2 to 7 mm. When the length L2 of the conductive part 3 is not less than the lower limit of the preferable range, it is easy to suppress leakage current. When the length L2 of the conductive part 3 is not more than the upper limit of the preferable range, it is possible to suppress deactivation of the plasma and the reactive species generated by the plasma.

It is preferable that the thickness of the conductive part 3 is equal to the thickness of the main tube 2.

The technical effects of the present embodiment are similar to those of the first embodiment, but since the conductive part 3 cannot be connected to the exterior material 16 and grounded, the first embodiment is superior in the effect of suppressing leakage current.

The conductive part 3 may be connected to the exterior material 16 using a separate electric wire, or may be directly connected to the ground wire.

Sixth Embodiment

Figure 6:
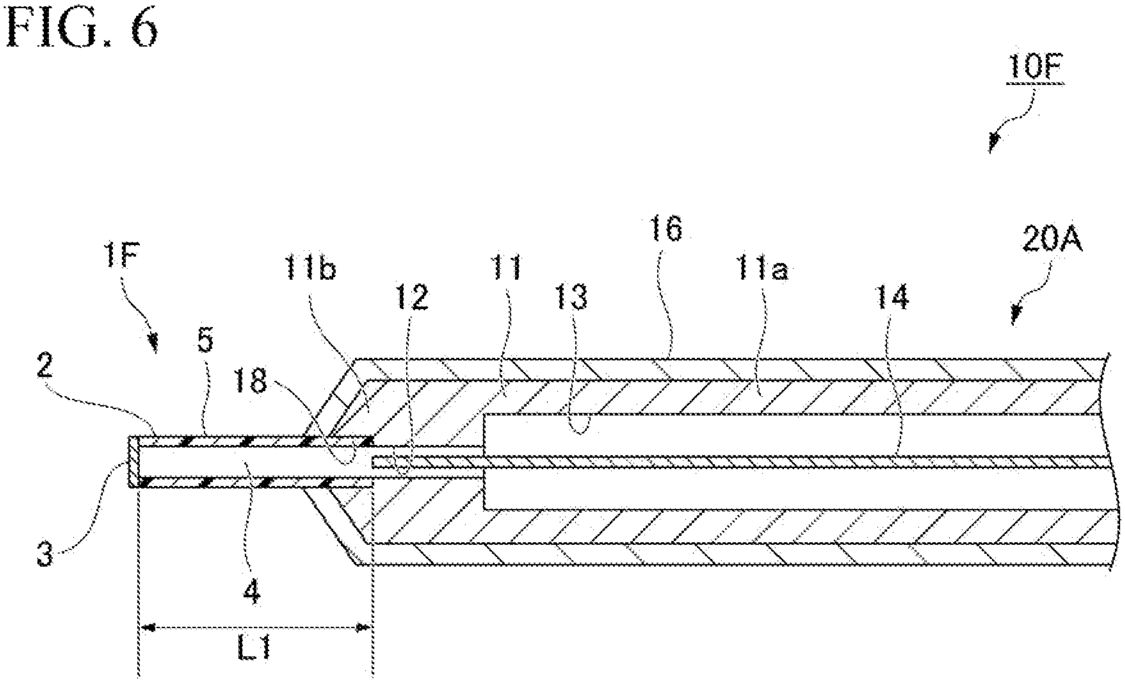
FIG. 6 is a partial cross-sectional view of an irradiation instrument according to a sixth embodiment of the present invention.

FIG. 6 is a partial cross-sectional view (longitudinal section) showing a plane along the axis of an irradiation nozzle 1F and an irradiation instrument 10F including the irradiation nozzle 1F according to the sixth embodiment of the present invention.

As shown in FIG. 6, the irradiation instrument 10F of the present embodiment includes an irradiation nozzle 1F and an irradiation instrument main body 20A, which is the same as the irradiation instrument main body 20A in the first embodiment.

The irradiation nozzle 1F is composed of a cylindrical main tube 2 and a mesh conductive part 3. The conductive part 3 is placed in contact with the end surface at the tip of the main tube 2 so as to close the tip of the main tube 2.

The main tube 2 in the present embodiment may be formed of a transparent non-conductive material or an opaque non-conductive material. When the main tube 2 is formed of a transparent non-conductive material, its portion which is not inserted into the irradiation instrument main body 20A becomes an exposed pan 5 through which the inside of the main tube 2 can be observed.

The main tube 2 in the present embodiment is the same as the main tube 2 in the first embodiment except that transparency is preferred, and the preferred examples thereof are also the same as in the first embodiment; therefore, detailed descriptions are omitted. As regards the type of metal used for forming the conductive part 3, the same descriptions as for the conductive part 3 of the first embodiment apply.

The thickness of the conductive part 3 is preferably 100 to 2000 μm, more preferably 100 to 500 μm. When the thickness of the conductive part 3 is not less than the lower limit of the preferable range, it, is easy to suppress leakage current. When the thickness of the conductive part 3 is not more than the upper limit of the preferable range, it is possible to suppress deactivation of the plasma and the reactive species generated by the plasma.

The mesh opening of the conductive part 3 is preferably 100 to 5000 μm, more preferably 1000 to 2000 μm.

The technical effects of the present embodiment are similar to those of the first embodiment, but since the conductive part 3 cannot be connected to the exterior material 16 and grounded, the first embodiment is superior in the effect of suppressing leakage current.

The conductive part 3 may be connected to the exterior material 16 using a separate electric wire, or may be directly connected to the ground wire.

Seventh Embodiment

Figure 7:
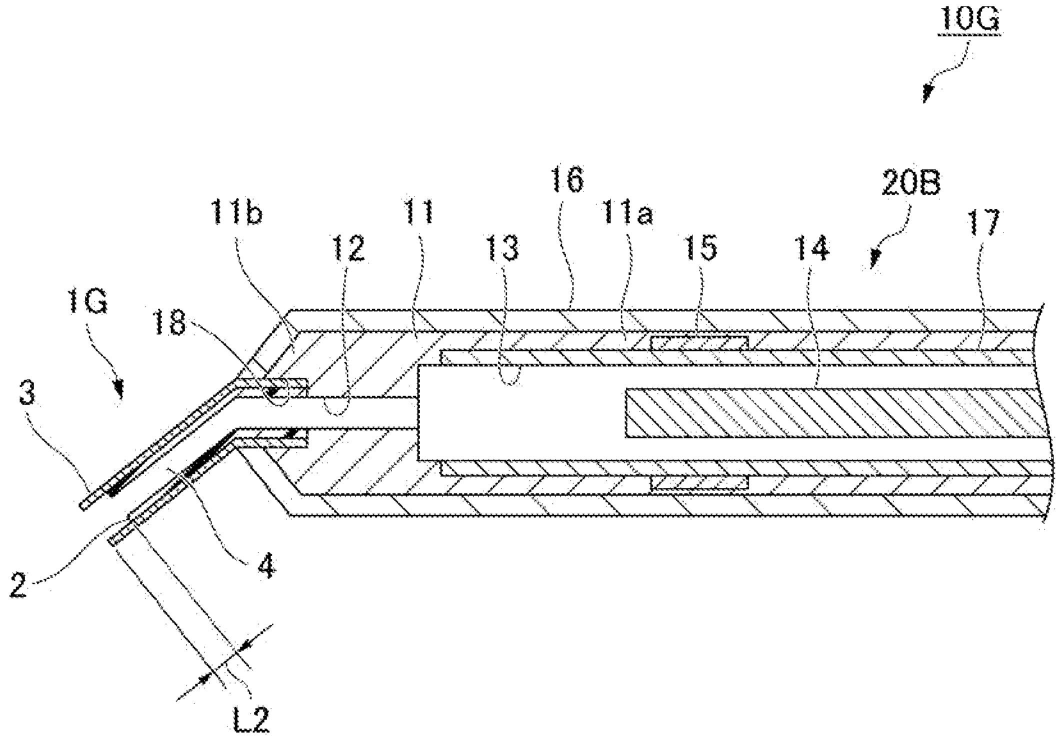
FIG. 7 is a partial cross-sectional view of an irradiation instrument according to a seventh embodiment of the present invention.

FIG. 7 is a partial cross-sectional view (longitudinal section) showing a plane along the axis of an irradiation nozzle 10 and an irradiation instrument 103 including the irradiation nozzle 1G according to the seventh embodiment of the present invention.

As shown in FIG. 7, the irradiation instrument 10G of the present embodiment includes an irradiation nozzle 1G and an irradiation instrument main body 208.

The irradiation nozzle 1G is composed of a bent cylindrical main tube 2 and a bent cylindrical conductive part 3. The conductive part 3 covers the entire outer surface of the main tube 2, and is in contact with the entire surface of the main tube 2 except for the exposed part 5 (including the outer surface at the tip of the main tube 2).

The rear end of the conductive part 3 is aligned with the rear end of the main tube 2, and the tip of the conductive part 3 projects further in the axial direction of the main tube 2 than the tip of the main tube 2.

The irradiation nozzle 1G is the same as in the case of the main tube 2 of the first embodiment except that it is bent between the portion inserted into the irradiation instrument main body 20B and the remaining portion not inserted into the irradiation instrument main body 208, and the preferred examples thereof are also the same as in the first embodiment; therefore, detailed descriptions are omitted.

With respect to the irradiation instrument main body 20B, an annular dielectric 17 is embedded in the cowling 11 at its portion facing the large-diameter flow channel 13, and a cylindrical outer electrode 15 is disposed further outside of the annular dielectric 17.

As the material of the annular dielectric 17, dielectric materials used in known plasma generators can be used. Examples of the material of the annular dielectric 17 include glass, ceramics, synthetic resins, and the like. The dielectric constant of the annular dielectric 17 is preferably as low as possible.

The inner electrode 14 is inserted along the tube axis of the cowling 11 from the rear end of the cowling 11 to a point slightly closer to the tip than the portion where the outer electrode 15 is positioned. As the material of the inner electrode 14, the same material as used in the inner electrode 14 of the first embodiment may be used.

The outer diameter of the inner electrode 14 can be appropriately set in consideration of the actual use of the instrument (that is, the size of the irradiation instrument 10G) and the like. In the case of an intraoral treatment apparatus, the outer diameter is preferably 0.5 to 20 mm, more preferably 1 to 10 mm. When the outer diameter is not less than the above lower limit, the inner electrode 14 can be easily manufactured. In addition, when the outer diameter is not less than the above lower limit, the surface area of the inner electrode 14 increases, so that plasma can be generated more efficiently, and healing etc. can be further promoted. When the outer diameter is not more than the above upper limit, plasma can be generated more efficiently and healing etc. can be further promoted without making the irradiation instrument 10G excessively large.

The distance between the outer surface of the inner electrode 14 and the inner surface of the annular dielectric 17 is preferably 0.05 to 5 mm, more preferably 0.1 to 1 mm. When the distance is not less than the above lower limit, a desired amount of plasma generating gas is allowed to flow easily. When the distance is not more than the above upper limit, plasma can be generated more efficiently and the temperature of the gas applied for medical use can be lowered.

As in the first embodiment, the inner electrode 14 functions as an application electrode that applies voltage to the plasma generating gas when connected to the power supply unit and supplied with power.

The material of the outer electrode 15 is not particularly limited as long as the material is electrically conductive, and metals used for electrodes of known plasma generating apparatuses can be used. Examples of the material of the outer electrode 15 include metals such as stainless steel, copper and tungsten, carbon, and the like.

The outer electrode 15 is connected to a ground wire of the power supply unit and functions as a ground electrode.

The exterior material 16 functions as a ground electrode similarly to the first embodiment, and when the conductive part 3 contacts the exterior material 16, the conductive portion 3 is grounded.

Since the other points of the exterior material 16 are the same as the exterior material 16 in the first embodiment, detailed explanations are omitted.

With respect to the irradiation instrument 10G of the present embodiment, plasma is generated when the plasma generating gas is introduced from the rear end of the large-diameter flow channel 13, and a voltage is applied between the inner electrode 14 and outer electrode 15 with the annular dielectric 17 sandwiched therebetween. In the present embodiment, a portion where the inner electrode 14 and the outer electrode 15 face each other becomes a plasma generation region. That is, the inner electrode 14, the outer electrode 15, and the annular dielectric 17 function as a plasma generating unit for forming a plasma region.

As in the case of the first embodiment, the inner diameter of the main tube 2 is preferably 0.1 to 2 times the diameter of the plasma generation region, more preferably 0.2 to 1.5 times, even more preferably 0.3 to 0.9 times.

However, the diameter of the plasma generation region in the present embodiment is the diameter of the flow channel in the portion where the inner electrode 14 and the outer electrode 15 face each other (diameter corresponding to an area of the portion excluding the portion where the inner electrode 14 is present from the inner diameter of the large-diameter flow channel 13).

In the present embodiment, since the irradiation nozzle 10 is bent, it is easy to deliver the reactive gas to the target. Other technical effects are the same as in the first embodiment.

Other Embodiments

The irradiation nozzle 1G of the seventh embodiment may be combined with the irradiation instrument main body 20A of the first embodiment.

Further, each of the irradiation nozzles of the second to sixth embodiments may be bent similarly to the irradiation nozzle 1G.

Any of the irradiation nozzles of the first to sixth embodiments may be combined with the irradiation instrument main body 20B of the seventh embodiment.

In the first to seventh embodiments, the conductive part is attached to the main tube, but the present invention is not limited thereto. For example, the conductive part may be a part independent of the main tube, and may be positioned at the tip of the conductive part and the main tube only when discharging the reactive gas.

The irradiation nozzle may be non-detachably fixed to the irradiation instrument main body. That is, the present invention also encompasses, as its one embodiment, an irradiation instrument configured such that the irradiation nozzle and the irradiation instrument main body are formed inseparably, i.e., an irradiation instrument in which the reactive gas discharge nozzle section formed in a non-detachable manner has the configuration of the irradiation nozzle described above.

Further, an irradiation instrument having a configuration in which the irradiation nozzle is accommodated within the irradiation instrument main body is also one embodiment of the present invention. That is, in the irradiation instrument of the present invention, the irradiation nozzle may be disposed inside the end portion of the irradiation instrument main body so as not to protrude from the tip of the irradiation instrument main body. In this instance, it is possible to adopt a configuration in which the tip of the main tube or the conductive part may be in contact with the periphery of the opening at the tip of the irradiation instrument main body.

Further, in each of the above embodiments, the main tube has a uniform inner diameter from the rear end to the tip, but it is also preferable that the main tube has an inner diameter decreasing from the rear end to the tip. With its inner diameter decreasing from the rear end to the tip, the main tube can increase the density of the reactive gas blown to the target. It is also possible to obtain the effect of increasing the flow rate of the reactive gas blown out from the irradiation outlet to increase the blow-out speed of the reactive gas. Further, since the inner space of the main tube is reduced, the inside of the main tube can be more easily filled with plasma, which provides another effect that deactivation of reactive species can be prevented. In this case, the ratio (B1/A1) of the inner diameter B1 at the tip of the main tube to the inner diameter A1 at the rear end of the main tube is preferably 0.1 to 1, more preferably 0.2 to 0.9, even more preferably 0.25 to 0.8. When the B1/A1 ratio is within this range, the above-mentioned effects can be surely obtained.

Further, in each of the embodiments described above, the exterior material 16 does not need to function as a ground electrode, and the exterior material 16 itself may be omitted.

Further, only the inner surface of the main tube 2 in each of the embodiments may be formed of a non-conductive material. Furthermore, a conductive part may exist in a part of the inner surface.

In addition, various alterations can be made as long as such alterations do not deviate from the gist of the present invention.

[Example of Specific Structure of Irradiation Nozzle]

The specific structure of the irradiation nozzle in one embodiment of the present invention is described below. That is, the irradiation nozzle of the present invention may have the following structure:

An irradiation nozzle for discharging a reactive gas containing one or both of plasma and a reactive species generated by the plasma, comprising:

a main tube with its inner surface being at least partially formed of a non-conductive material; and a conductive part formed of a conductive material.

wherein the conductive part satisfies one or both of (1) and (2):

(1) at least part of the conductive part is located at a tip of the main tube; and (2) the conductive part is located on part of the inner surface of the main tube.

Regarding the first to seventh embodiments illustrated above, the fourth embodiment satisfies both of the requirements (1) and (2) above, and the other embodiments satisfy only the requirement (1).

Regarding the above requirement (2), (at least a part of) the conductive part does not necessarily need to be located at the tip of the main tube. In this instance, it is preferable that the tip of the conductive part is located closer to the tip of the main tube than the midpoint in the axial direction of the main tube, and it is more preferable that the tip of the conductive part is located within 25% from the tip of the main tube, with the tip of the main tube in the axial direction of the main tube being defined as the starting point (0%) and the total length in the axial direction of the main tube being defined as 100%. Regarding the configurations other than this point, the descriptions regarding the first to seventh embodiments can be applied as they are, but particularly preferred configurations are described below.

As mentioned above, "at least" in the expression "inner surface being at least partially formed of a non-conductive material" means preferably 5) 1% or more, more preferably 80% or more, even more preferably 99% or more of the total area of the inner surface of the main tube, but it is particularly preferable that the entire inner surface (100%) of the main tube is formed of a non-conductive material. This can improve the effect of preventing plasma deactivation.

It is preferable that the conductive part covers part or all of an end surface at the tip of the main tube or an outer surface of the main tube and has a protrusion protruding beyond the tip of the main tube in an axial direction of the main tube. This configuration applies to the first to third and fifth to seventh embodiments.

It is preferable that the protrusion has an annular shape, and the diameter of the protrusion decreases in the axial direction of the main tube. In this instance, the ratio (B2/A2) of the inner diameter B2 at the tip of the conductive part (projection) to the inner diameter A2 at the tip of the main tube is preferably 0.1 to 1, more preferably 0.2 to 09, even more preferably 0.25 to 0.8. When the B/A ratio is within this range, the density of the reactive gas applied to the target can be increased. In addition, by increasing the flow rate of the reactive gas blown out from the irradiation outlet, the blow-out velocity of the reactive gas can be increased.

Further, as described above, the irradiation nozzle of the present invention can be used in an irradiation instrument comprising the irradiation nozzle of the present invention and an irradiation instrument main body, wherein the irradiation instrument main body has therein a plasma generation region where plasma is generated.

Preferred examples of the irradiation instrument include:

an irradiation instrument, wherein the irradiation nozzle has an attach-detach mechanism that is attached to and engages with the irradiation instrument main body, wherein a rear end of the main tube is in contact with a periphery of an opening at a tip of the irradiation instrument main body.

Figure 8:
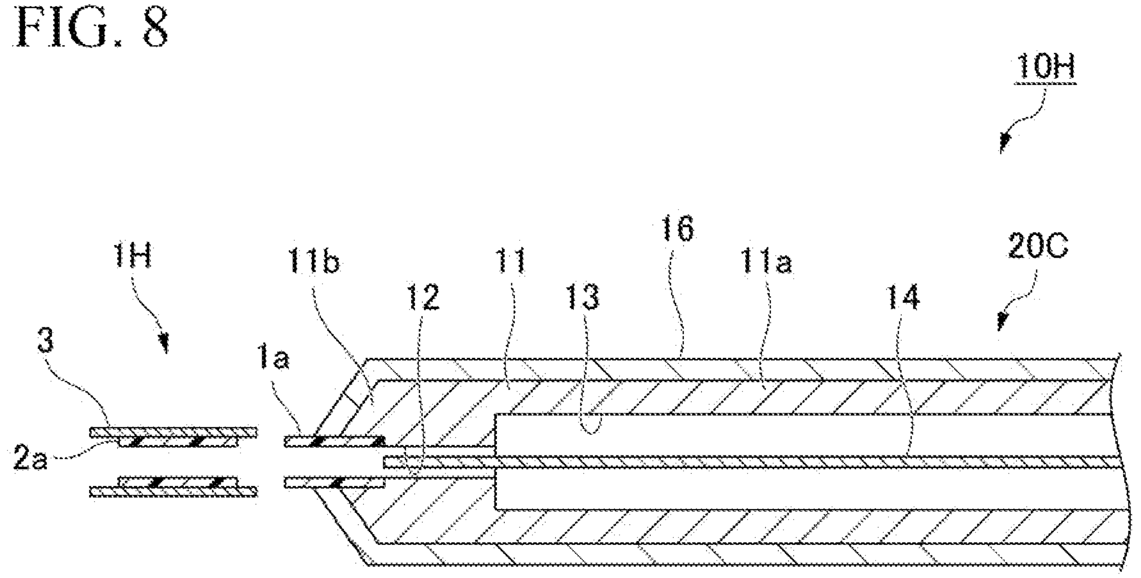
FIG. 8 is a partial cross-sectional view of an irradiation instrument according to another embodiment of the present invention.

An example of such an irradiation instrument is shown in FIG. 8.

The irradiation instrument 10H shown in FIG. 8 includes an irradiation nozzle 11H and an irradiation instrument main body 20C. FIG. 8 shows a state before the irradiation nozzle 1H and the irradiation instrument main body 20C are combined. The irradiation instrument 10H of the present embodiment has the advantage that a commercially available irradiation instrument can be used.

In the example of FIG. 8, the irradiation instrument main body 20C has a nozzle 1*a* formed only of a non-conductive material at an opening at its tip. The rear end of the main tube 2*a* of the irradiation nozzle 1H of the present invention is disposed so as to conic into contact with the tip of the nozzle 1*a* of the irradiation instrument main body 20C.

The nozzle 1*a* may have the same structure as the main tube 2 of the first to seventh embodiments, but the main tube 2*a* and the nozzle 1*a* may be formed of different materials. For example, the main tube 2*a* may be formed of a resin, while the nozzle 1*a* may be made of a ceramic. In this instance, since the nozzle 1*a* is formed of a ceramic and the main tube 2*a* is formed of a resin, it is possible to prevent the nozzle 1*a* front being damaged (cracked when the rear end of the main tube 2*a* is brought into contact with the nozzle 1*a* to form the irradiation nozzle 1H. Further, for ensuring this damage prevention effect, it is preferable that the hardness of the resin used in the main tube 2*a* is 50 to 85 in terms of Type D hardness specified in JIS-K7215.

In addition, with the irradiation nozzle 1H and the irradiation instrument main body 20C being combined, the main tube 2*a* and the nozzle 1*a* can be collectively regarded as the main tube 2.

As regards the attach-detach mechanism (not shown) that is attached to and engages with the irradiation instrument main body 20C, known ones can be employed. Examples of the attach-detach mechanism include a mechanism that uses the nozzle 1*a* having a fitting hole (female thread) at its tip, and the irradiation nozzle 1H having a fitting protrusion (male thread) at its rear end, wherein the fitting hole and the fitting protrusion are fitted together. In the example of FIG. 8, a fitting protrusion (male thread) is provided on the inner surface of the conductive part at the rear end of the irradiation nozzle 1H.

Regarding the irradiation nozzle 1H, the descriptions regarding the irradiation nozzles 1A to 1G in the first to seventh embodiments can be applied except for the attach-detach mechanism.

The irradiation instrument main body 20C may have the same configuration as the irradiation instrument main body 20A in the first embodiment, except for the nozzle 1*a*. Further, a commercially available irradiation instrument can also be used as the irradiation instrument main body 20C.

<Plasma Treatment Apparatus>

Figure 9:
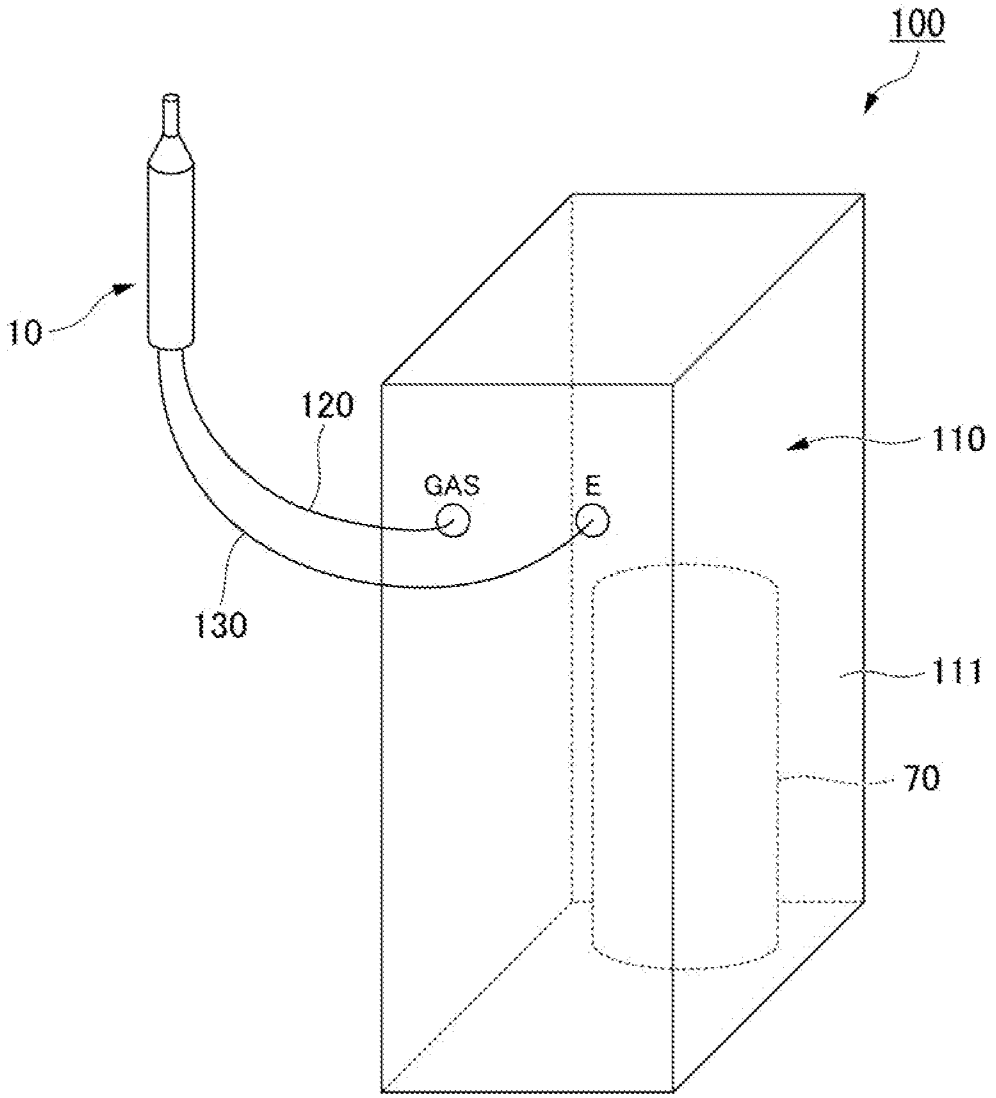
FIG. 9 is a schematic view showing a plasma treatment apparatus according to one embodiment of the present invention.
Figure 10:
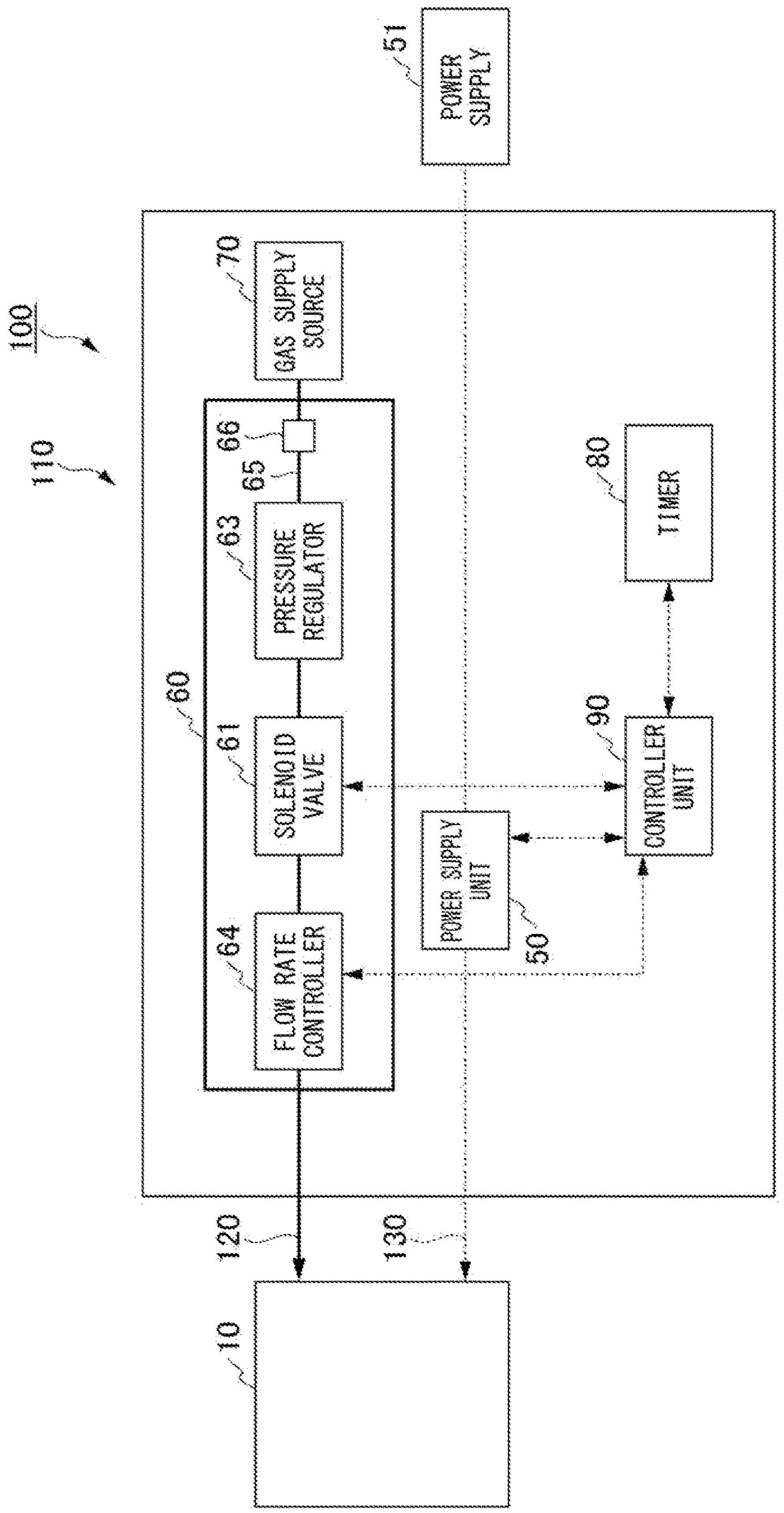
FIG. 10 is block diagram showing a schematic configuration of a plasma treatment apparatus according to one embodiment of the present invention.

FIG. 9 is a schematic view showing a plasma treatment apparatus 100 according to the present embodiment. FIG. 10 is block diagram showing a schematic configuration of the plasma treatment apparatus 100 according to the present embodiment.

As shown in FIG. 9, the plasma treatment apparatus 100 of the present embodiment includes an irradiation instrument 10, a supply unit 110, a gas conduit 120, an electricity supply line 130, and a gas supply source 70 accommodated in a housing Ill of the supply unit 110. The gas supply source 70 contains a plasma generating gas.

The supply unit 110, as shown in FIG. 10, supplies electricity and plasma generating gas to the irradiation instrument 10.

In order to supply power to the irradiation instrument 10, the supply unit 110 has a power supply unit 50 connected to a power supply 51 (for example, a 100 V household power supply, etc.). The power supply unit 50 supplies power to the irradiation instrument 10 connected via the electricity supply line 130.

When the irradiation instrument 10 is the irradiation instrument 10 (10A to 10F) of the first to sixth embodiments or the irradiation instrument 10I described above, the power supply unit 50 applies an alternating voltage between the inner electrode 14 and the exterior material 16. When the irradiation instrument 10 is the irradiation device 10G of the seventh embodiment, the power supply unit 50 applies an alternating voltage between the inner electrode 14 and the outer electrode 15.

The alternating voltage applied is preferably 3 kVpp or more and 20 kVpp or less. In this context, the unit "Vpp (peak-to-peak voltage)" representing the alternating voltage means a potential difference between the highest value and the lowest value of the alternating voltage waveform.

The frequency of the alternating voltage is preferably 0.5 kHz or more and less than 40 kHz, more preferably 10 kHz or more and less than 30 kHz, even more preferably 15 kHz or more and less than 25 kHz, particularly preferably 18 kHz or more and less than 22 kHz.

With the frequency of the alternating voltage set to less than the above upper limit value, the temperature of the generated plasma can be suppressed low. With the frequency of the alternating voltage set to equal or exceed the above lower limit value, plasma can be generated more efficiently.

In order to supply plasma generating gas to the irradiation instrument 10, the supply unit 110 has a gas supply section 60.

The gas supply section 60 includes a gas conduit 65 that connects the gas supply source 70 and the gas conduit 120. The gas conduit 65 is provided with a solenoid valve 61, a pressure regulator 63, and a flow rate controller 64 (flow rate adjustment section). The flow rate controller 64 and the solenoid valve 61 are connected to a controller unit 90.

The solenoid valve 61 switches between opening and closing to start and stop the supply of plasma generating gas front the gas supply source 70 to the irradiation instrument 10. In the example shown in the drawing, the solenoid valve 61 is not configured to enable adjustment of the valve opening degree, but is configured to enable only switch between opening and closing. However, the solenoid valve 61 may also be configured to enable adjustment of the valve opening degree.

The pressure regulator 63 is positioned between the solenoid valve 61 and the supply source 70. The pressure regulator 63 lowers the pressure of the plasma generating gas from the supply source 70 to the solenoid valve 61 (i.e., the pressure regulator 63 reduces the pressure of the plasma generating gas).

The flow rate controller 64 is disposed between the solenoid valve 61 and the gas conduit 120. The flow rate controller 64 adjusts the flow rate (supply rate per unit time) of the plasma generating gas having passed through the solenoid valve 61. For example, the flow rate controller 64 adjusts the flow rate of the plasma generating gas to 1 to 10 L/min.

A joint 66 is provided at the end of pipe 65 on the supply source 70-side. The supply source 70 is detachably attached to the joint 66. The attachment or detachment of the supply source 70 to or from the joint 66 allows for replacement of the supply source 70 while leaving the gas supply unit fixed to the housing 111.

The controller unit 90 is composed of an information processing unit, in other words, the controller unit 90 is equipped with a CPU (central processing unit), a memory and an auxiliary storage device, which are connected by buses. The controller unit 90 operates by executing a program. The controller unit 90 may be built into the housing 111 or may be provided separately from the housing 111.

An operation switch (not shown) is electrically connected to the controller unit 90. The operation switch is provided at an appropriate location on the irradiation instrument 10, the housing 111, and the like. A foot switch may also be used.

When the operation switch is turned on, an electrical signal is sent from the operation switch to the controller unit 90. When the controller unit 90 receives the electrical signal, the controller unit 90 activates the solenoid valve 61 and the flow controller 64, and allows the power supply unit 50 to supply power to the irradiation instrument 10. Thus, the plasma generating gas is sent to the irradiation instrument 10, and a voltage is applied to the plasma generating gas by the inner electrode 14 within the irradiation instrument 10.

The supply unit 110 in the present embodiment has a timer 80. This enables an operation that, when a predetermined irradiation time (time set by the timer 80) has elapsed, the controller unit 90 stops at least one of the supply of plasma generating gas and the supply of electricity to the irradiation instrument 10, to thereby automatically terminate discharge of the reactive gas.

Examples of targets to be irradiated by the plasma treatment apparatus 100 include cells, biological tissues, living organisms, organic materials (e.g., resins, etc.), and inorganic materials (e.g., ceramics, metals, etc.).

Examples of the living tissue include various internal organs, epithelial tissues covering the body surface and the inner surfaces of the body cavity, periodontal tissues such as gums, alveolar bone, periodontal ligament and cementum, teeth, hones and the like.

The whole bodies of organisms may be any of mammals such as humans, dogs, cats, pigs and the like; birds; fishes and the like.

Examples of the plasma generating gas include noble gases such as helium, neon, argon and krypton; nitrogen; oxygen; and air. With respect to these gases, a single type thereof may be used individually or two or more types thereof may be used in combination.

The plasma generating gas preferably contains nitrogen gas as a main component. In this context, the nitrogen gas being contained as a main component means that the amount of the nitrogen gas contained in the plasma generating gas is more than 50% by volume. That is, the amount of the nitrogen gas contained in the plasma generating gas is preferably more than 50% by volume, more preferably 70% by volume or more, still more preferably 80 to 100% by volume, particularly preferably 90 to 100% by volume. The gas component other than nitrogen in the plasma generating gas is not particularly limited, and examples thereof include oxygen and a noble gas.

Further, it is also a preferred embodiment of the present invention that the plasma generating gas has a rare gas as a main component. Argon, helium, etc. are preferable as the rare gas. The amount of the rare gas in the plasma generating gas is the same as in the above-mentioned case of nitrogen. Since rare gases easily turn into plasma, the use of rare gases as the plasma generating gas has the advantage that the reactive gas flow channel is more easily filled with plasma, and the reactive species are less likely to be deactivated. The gas components other than the rare gas in the plasma generating gas are not particularly limited, and examples thereof include oxygen, nitrogen, and the like.

The temperature of the reactive gas discharged from the irradiation instrument 10 is preferably 50° C. or less, more preferably 45° C. or less, even more preferably 40° C. or less.

When the temperature of the reactive gas discharged from the irradiation instrument 10 is not more than the upper limit value, the temperature of the irradiation target can be easily adjusted to 40° C. or less. By keeping the temperature of the irradiation target at 40° C. or less, stimulus to the irradiation target can be reduced even when the irradiation target is an affected part.

The lower limit value of the temperature of the reactive gas is not particularly limited, and is, for example, 10° C. or more.

The temperature of the reactive gas is a temperature value of the reactive gas at the tip of the irradiation nozzle measured by a thermocouple.

The distance (irradiation distance) from the tip of the irradiation nozzle to the target is preferably, for example, 0.01 to 10 mm. When the irradiation distance is not less than the above lower limit value, the temperature at the tip of the irradiation nozzle can be lowered, and the stimulus to the tip of the irradiation nozzle can be further reduced. When the application distance is not more than the above upper limit value, the effect of healing and the like can be further enhanced.

The temperature of the irradiation target positioned at a distance of 1 mm or more and 10 mm or less from the tip of the irradiation nozzle is preferably 40'C or less. When the temperature of the irradiation target is 40° C. or less, stimulus to the irradiation target can be reduced. The lower limit value of the temperature of the irradiation target is not particularly limited, and is, for example, 10° C. or more.

The temperature of the target is adjusted by controlling, in combination, the alternating voltage applied to the inner electrode 14, the discharge amount of the tractive gas, and the like.

Examples of the reactive species (radicals etc.) contained in the reactive gas include hydroxyl radicals, singlet oxygen, ozone, hydrogen peroxide, superoxide anion radicals, nitric oxide, nitrogen dioxide, peroxynitrite, dinitrogen trioxide and the like. The type of the reactive species contained in the reactive gas can be further controlled by, for example, the type of the plasma generating gas.

The flow rate of the reactive gas discharged from the irradiation instrument 10 is preferably 1 L/min to 10 L/min.

When the flow rate of the reactive gas is not less than the above lower limit value, the effect of the reactive gas acting on the irradiation target can be sufficiently enhanced. When the flow rate of the reactive gas is less than the above upper limit value, excessive increase in the temperature of the reactive gas at the irradiation target can be prevented. In addition, when the irradiation target is wet, rapid drying of the irradiation target can be prevented. Furthermore, when the irradiation target is an affected part of a patient, stimulus inflicted on the patient can be suppressed.

In the plasma treatment apparatus 100, the flow rate of the reactive gas blown to the target can be adjusted by the supply amount of the plasma generating gas to the irradiation instrument 10.

The plasma treatment apparatus 100 of the present embodiment is particularly useful as an intraoral treatment apparatus or a dental treatment apparatus. The plasma treatment apparatus 100 of the present embodiment is also suitable as an animal treatment apparatus (for example, a treatment apparatus for treating the oral cavity of animals other than humans).

Since the plasma treatment apparatus 100 of the present embodiment includes the irradiation instrument 10 of the present invention, it is possible to deliver a sufficient amount of reactive species to the target while suppressing pain to the target such as the affected area, and it is also possible to prevent the tip of the irradiation instrument from becoming thick so as to provide a plasma treatment apparatus that can irradiate narrow areas such as the inside of the oral cavity.

EXAMPLES

<Evaluation Method>

In each of the Examples, the leakage current and singlet oxygen density were measured as follows.

[Leakage Current]

Reactive gas is applied for 60 seconds to a copper foil to which a human body-simulating resistor described in the medical standard IEC60601-1 is connected. In this process, the distance from the tip of the irradiation nozzle to the copper foil to be irradiated is set to 3.0 mm (in Comparative Example 1, the distance from the tip of the irradiation instrument main body 20A to the copper foil to be irradiated is set to 12.0 mm). The maximum value of the effective value of the current flowing through the human body-simulating resistor circuit is defined us the leakage current due to the reactive gas.

[Singlet Oxygen Density]

Reactive gas is blown to 0.4 mL of a 0.1 mol/L solution of TPC (2,2,5,5-tetramethyl-3-pyrroline-3-carboxamide) for 30 seconds. In this process, the distance from the tip of the irradiation nozzle to the liquid level is set to 3.0 mm (in Comparative Example 1, the distance from the tip of the irradiation instrument main body 20A to the liquid level is set to 12.0 mm). With respect to the solution to which the reactive gas has been applied, a singlet oxygen concentration is measured by electron spin resonance (ESR) method.

EXAMPLES AND COMPARATIVE EXAMPLES

Comparative Example 1

Reactive gas was discharged directly from the irradiation instrument main body 20A, and the leakage current and singlet oxygen density were determined. The results are shown in Table 1.

In the irradiation instrument main body 20A, both the inner electrode 14 and the exterior material 16 were made of stainless steel.

The length, etc. of parts of the irradiation instrument main body 20A were as follows.

Inner diameter at the tip of the outlet: 2.5 mm.

Length from the tip of the inner electrode 14 to the tip of the outlet: 10 mm.

As the plasma generating gas, Ar gas was supplied at 4.5 L/min. An alternating voltage of 1 kVpp at 1 MHz was applied to the inner electrode 14.

Example 1

The same procedure as in Comparative Example 1 was repeated except that the irradiation nozzle attached to the irradiation instrument main body 20A was configured such that a metal tube (conductive part) covered the entire outer surface of a resin tube and protruded from the tip of the resin tube in its axial direction, to allow reactive gas to be discharged, and determine the leakage current and the singlet oxygen density. The results are shown in Table 1.

The dimensions of parts of the irradiation nozzle were as follows.

Resin tube: made of PFA, length 7 mm, inner diameter 2 mm, thickness 500 μm.

Metal tube: made of Cu, length 9 mm, inner diameter 3 mm, thickness 100 μm.

Length from the tip of irradiation instrument main body 20A to the tip of resin tube: 7 mm.

Length from the tip of irradiation instrument main body 20A to the tip of metal tube: 9 mm.

Comparative Example 2

The same procedure as in Comparative Example 1 was repeated except that the irradiation nozzle attached to the irradiation instrument main body 20A was a resin tube, to allow reactive gas to be discharged, and determine the leakage current and the singlet oxygen density. The results are shown in Table 1.

The dimensions of parts of the irradiation nozzle were as follows.

Resin tube: made of PFA, length 9 mm, inner diameter 2 mm, thickness 500 μm.

Length from the tip of irradiation instrument main body 20A to the tip of resin tube: 9 mm.

Comparative Example 3

The same procedure as in Comparative Example 1 was repeated except that the irradiation nozzle attached to the irradiation instrument main body 20A was a metal tube, to allow reactive gas to be discharged, and determine the leakage current and the singlet oxygen density. The results are shown in Table 1.

The dimensions of parts of the irradiation nozzle were as follows.

Metal tube: made of Cu, length 9 mm, inner diameter 2 mm, thickness 100 μm.

Length from the tip of irradiation instrument main body 20A to the tip of metal tube: 9 nm.

Comparative Example 4

The same procedure as in Comparative Example 1 was repeated except that the irradiation nozzle attached to the irradiation instrument main body 20A was a resin tube, to allow reactive gas to be discharged, and determine the leakage current and the singlet oxygen density. The result are shown in Table 1.

The dimensions of parts of the irradiation nozzle were as follows.

Resin tube: made of PFA, length 9 mm, inner diameter 4 mm, thickness 1000 μm.

Length from the tip of irradiation instrument main body 20A to the tip of resin tube: 9 mm.

TABLE 1

| | | Comparative Example 1 | Example 1 | Comparative Example 2 | Comparative Example 3 | Comparative Example 4 |
|---|---|---|---|---|---|---|
| Leakage current | μA | 8.9 | 1 or less | 101.3 | 1 or less | 5.83 |
| Singlet oxygen concentration | μm | 5.092 | 11.8 | 13.43 | 5.179 | 4.625 |

As shown in Table 1, when the irradiation nozzle having a conductive pan connected to the tip of the resin tube was used as in the Examples, the leakage current was smaller than in Comparative Example 1 not using an irradiation nozzle, and it was also possible to increase the singlet oxygen density.

On the other hand, in Comparative Example 2 using only a resin tube, although the singlet oxygen density was increased, an extremely large leakage current occurred. Further, in Comparative Example 2 using only a metal tube, although the leakage current was reduced, the singlet oxygen density was low. Furthermore, in Comparative Example 4, the inner diameter of the irradiation nozzle was too large, resulting in almost the same results as when no irradiation nozzle was used.

REFERENCE SIGNS LIST

1A, 1B, 1C, 1D, 1D, 1F, 1G, 1*a* Irradiation nozzle
2, 2*a* Main tube
3 Conductive part
4 Reactive gas flow channel
5 Exposed part
10, 10A, 10B, 10C, 10D, 10E, 10F, 10G, 10H Irradiation instrument
11 Cowling
12 Small-diameter flow channel
13 large-diameter flow channel
18 Fitting hole
14 Inner electrode
15 Outer electrode
16 Exterior material
17 Annular dielectric
20A, 20B, 20C Irradiation instrument main body
50 Power supply unit
60 Gas supply unit
70 Gas supply source
90 Controller unit
100 Plasma treatment apparatus
110 Supply unit
111 Housing
120 Gas conduit
130 Electricity supply line

The invention claimed is:

1. An irradiation instrument comprising:

an irradiation nozzle for discharging a reactive gas including at least one of plasma or a reactive species generated by the plasma;

an irradiation instrument main body including therein a plasma generation region where an inner electrode and an outer electrode face each other, a main tube including an inner surface which is entirely formed of a non-conductive material; and a conductive part at a tip of the main tube, wherein:

at least part of the conductive part is configured to come into contact with the reactive gas discharged from the tip of the main tube;

the main tube is downstream of the plasma generation region toward a tip end of the irradiation nozzle; and the main tube is free of any electrode therein.

2. The irradiation instrument according to claim 1, wherein the conductive part covers at least part of an outer surface of the main tube and protrudes beyond the tip of the main tube in an axial direction of the main tube.

3. The irradiation instrument according to claim 1, wherein the main tube is formed of a transparent material, and at least part of an outer surface of the main tube is not covered with any material so as to form an exposed part exposed to an outside of the main tube, so that an inside of the main tube is observable through the exposed part.

4. The irradiation instrument according to claim 3, wherein the conductive part covers all of the outer surface of the main tube except for the exposed part and protrudes beyond the tip of the main tube in an axial direction of the main tube.

5. The irradiation instrument according to claim 1, wherein the conductive part is grounded.

6. The irradiation instrument according to claim 1, wherein the irradiation nozzle is detachable from the irradiation instrument main body.

7. A plasma treatment apparatus comprising:

the irradiation instrument according to claim 1;

a gas supply unit configured to supply plasma generating gas to the irradiation instrument main body; and a power supply unit configured to supply power to the irradiation instrument main body.

* * * * *